United States Patent [19]

Cabestany et al.

[11] Patent Number: 4,590,249

[45] Date of Patent: May 20, 1986

[54] CATIONIC AMPHOLYTIC TETRAPOLYMERS AND COSMETIC COMPOSITIONS CONTAINING THEM

[75] Inventors: Jean Cabestany, Stains; Daniel Siegel, Montesson; Roland Righetti, Le Chesnay, all of France

[73] Assignee: Societe Francaise Hoechst, Puteaux, France

[21] Appl. No.: 659,539

[22] Filed: Oct. 10, 1984

[30] Foreign Application Priority Data

Oct. 19, 1983 [FR] France ............... 83 16621

[51] Int. Cl.⁴ .............. A61K 7/06; A61K 7/09; C08F 220/58
[52] U.S. Cl. .................... 526/287; 424/70; 424/72
[58] Field of Search .................. 526/287

[56] References Cited

U.S. PATENT DOCUMENTS

| | | | |
|---|---|---|---|
| 3,937,802 | 2/1976 | Fujimoto et al. | 526/287 |
| 4,075,183 | 2/1978 | Kawakami et al. | 526/287 |
| 4,171,418 | 10/1979 | Barua et al. | 526/287 |
| 4,460,569 | 7/1984 | Strasilla et al. | 526/287 |

*Primary Examiner*—Harry Wong, Jr.
*Attorney, Agent, or Firm*—Sheridan Neimark; Karl W. Flocks

[57] ABSTRACT

The invention relates to new cationic ampholytic water-soluble tetrapolymers for cosmetic compositions for treating keratinous fibers and resulting from copolymerization of:

a moles of acrylamide, AAM, b moles of 2-acrylamido-2-methyl-propane sulfonic acid, AMPS, b moles of a basic monomer selected from the three following monomers: dimethylaminoethyl acrylate, ADAME, N-(3-dimethylamino-1-propyl) acrylamide, DMAPA, N-(3-dimethylamino-1-propyl) methacrylamide, DMAPMA, c moles of a cationic monomer selected from the four following monomers:

N,N,N-3-trimethylacrylamido-propanaminium chloride, APTAC,

N,N,N-3-trimethylmethacrylamido-propanaminium chloride, MAPTAC,

N,N,N-2-trimethylacryloyloxy-ethanaminium chloride, CMA, dimethylaminoethyl acrylate hydrochloride, CHA, with the following relations:

$a + 2b + c = 100$ $30 < a < 75$ $10 < b < 25$ $5 < c < 20.$

4 Claims, No Drawings

CATIONIC AMPHOLYTIC TETRAPOLYMERS AND COSMETIC COMPOSITIONS CONTAINING THEM

This invention relates to cationic ampholytic tetrapolymers, their application to the treatment of keratinous fibers and compositions containing them.

It is known to use anionic, cationic polymers, ionomers or their mixtures in cosmetic compositions for treating keratinous fibers.

In spite of their interest, such compositions do not provide simultaneously and at little cost all the qualities desirable for present day customers.

As a matter of fact, and more particularly, in treating hair the user desires to have available at the least price and for current usage, performing compositions stable in the course of time, compatible with the anionic surfactants commonly used in such applications, such as sodium laurylethersulfate, giving bright, nervous, not fishy, not electric hair of soft touch, easy to do, of good behaviour, and conferring volume to the hair.

However, the Applicants have discovered compositions for treating keratinous fibers corresponding to the wishes and requirements of customers.

This purpose is reached due to the use of novel cationic water-soluble ampholytic tetrapolymers in the compositions according to the invention.

These novel cationic water-soluble ampholytic tetrapolymers which are the object of this invention can be represented in a very schematic manner by the following general formula:

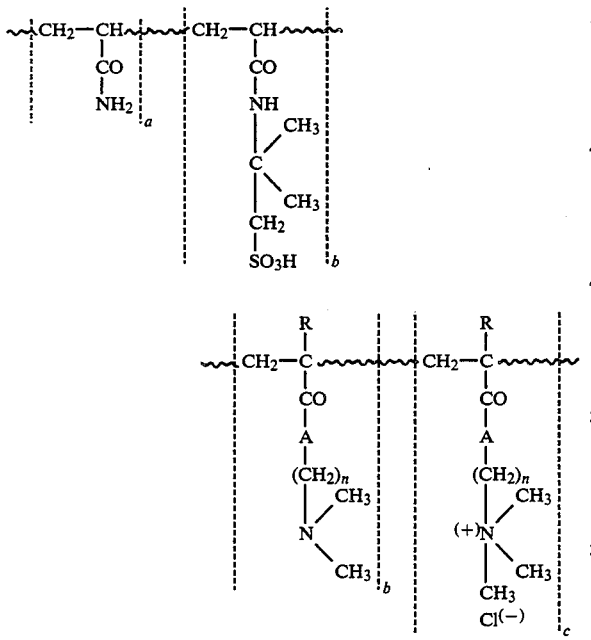

in which A represents an oxygen atom or an NH group, R represents a hydrogen atom or a methyl group when A represents an NH goup, and only a hydrogen atom when A represents an oxygen atom, n is equal to 2 when A represents an oxygen atom and n is equal to 3 when A represents an NH group, with letters a, b, c representing the molar percentage of each monomer used, and corresponding to the following relations:

$a + 2b + c = 100$ $30 < a < 75$ $10 < b < 25$ $5 < c < 20$

The object of this invention is more particularly tetrapolymers such as defined above characterized moreover in that they result from copolymerization according to means known in themselves of the four known polymers belonging to the four following classes of monomers with the following molar percentages:

1 a % of acrylamide, AAM 2 b % of 2-acrylamido-2-methyl-propane sulfonic acid, AMPS, 3 b % of a basic monomer chosen among the following three monomers:
  dimethylaminoethyl acrylate, ADAME,
  N-(3-dimethylamino-1-propyl)-acrylamide, DMAPA,
  N-(3-dimethylamino-1-propyl)-methacrylamide, DMAPMA, 4 c % of a cationic monomer selected from the four following monomers:
  N,N,N-3-trimethylacrylamido-propanaminium chloride, APTAC;
  N,N,N-3-trimethylmethacrylamido-propanaminium chloride, MAPTAC;
  N,N,N-2-trimethylacryloyloxy-ethanaminium chloride, CMA;
  dimethylaminoethyl acrylate hydrochloride, CHA.

Letters a, b, c have the above meanings.

This means in other terms that in the cationic ampholytic tetrapolymers according to the invention the molar percentage of acrylamide is between 30 and 75%, the molar percentages of 2-acrylamido-2-methyl-propane sulfonic acid and basic monomer are equal and between 10 and 25% and the molar percentage of cationic monomer is between 5 and 20%.

The object of this invention is more especially:
a tetrapolymer corresponding to the above mentioned general definition characterized moreover in that it contains in molar proportions, 75% of acrylamide, 10% of 2-acrylamido-2-methyl-propanesulfonic acid, 10% of N-(3-dimethylamino-1-propyl)-methacrylamide and 5% of N,N,N-3-trimethylmethacrylamido-propanaminium chloride; and a tetrapolymer corresponding to the above mentioned general definition further characterized in that it contains in molar proportions: 40% of acrylamide, 20% of 2-acrylamido-2-methyl-propanesulfonic acid, 20% of N-(3-dimethylamino-1-propyl)-methacrylamide, and 20% of N,N,N-3-trimethylmethacrylamido-propanaminium chloride.

The reactivity ratios $r_1$ and $r_2$ of these acid, basic or aminium monomers with acrylamide are favourable to a homogeneous copolymerization For the AAM-AMPS couple $r_1 = 1$ and $r_2 = 0.52$ (C. L. Mc CORMICK et Al. J.POLYMER Sci.C, 1982, 20, 817–838), for the AAM-ADAME couple salified or quaternized, $r_1 = 0.7$–$0.8$ and $r_2 = 0.55$–$0.66$ (U.S. Pat. No. 4,396,752), for the AAM-DMAPMA couple, $r_1 = 0.47$ and $r_2 = 0.98$, and for the AAM-MAPTAC couple, $r_1 = 0.51$ and $r_2 = 1.08$ (as determined according to the method of T. KELEN et Al. J.POLYMER Sci.C, 1977, 15, 3047–3074).

The tetrapolymers according to this invention are readily obtained from the previously cited monomers by radicalar copolymerization in aqueous homogeneous deoxygenated phase realized in an inert atmosphere and at a slightly acid pH generally included between 4 and 5 to prevent any risk of hydrolysis of the possibly present ester functions.

The initial weight concentration in monomers (Co) may vary from 10 to 40% and the conventional water-soluble initiators acting by thermal homolysis such as ammonium persulfate can be used.

The copolymerization is effected hot generally at about 60°–80° C., then when it is completed, the reaction aqueous solution previously cooled at the ambient temperature is neutralized if necessary at pH=6.7 with diluted ammonia and finally the obtained solution is possibly protected by addition of known bactericides and fungicides at the conecentration usually employed in cosmetology.

The so obtained tetrapolymer in aqueous solution presents an intrinsic viscosity determined at 20° C. in a molar solution of sodium chloride of between 1 and 5 dl/g. Although by modifying Co and the initiator rate of copolymerization one can obtain as desired either a higher intrinsic viscosity or a smaller intrinsic viscosity, in order for an aqueous solution of the tetrapolymer according to the invention to be useful for treating keratinous fibers, it is necessary that it be sufficiently viscous to remain on the fibers and sufficiently fluid to efficiently moisten the fibers.

Experience shows that the quantity of tetrapolymers according to the invention to be introduced into the compositions or formulations according to the invention depends on the specific results which one desires to reach. Generally, this quantity must constitute a proportion in the order of about 0.1 to 5% by weight as expressed in dry materials relative to the total weight of the aqueous composition.

Although the cationic water-soluble ampholytic tetrapolymers in accordance with this invention constitute the essential active ingredients of the compositions in accordance with this invention, such compositions may also contain other ingredients which may in particular improve organoleptic properties or facilitate application thereof.

Thus, it is also suitable within the scope of this invention to incorporate into the compositions according to the invention one or more usual or known constituents of such compositions such as for example perfumes, colorants that may have the function of coloring the composition itself or the keratinous fibers, preserving agents, sequestering agents, thickeners, softeners, foam synergistic agents, foam stabilizers, solar filters, peptizing agents, as well as anionic, cationic, amphoteric, non ionic surfactants, or their mixtures.

The carrier or vehicle associated with the composition according to the invention is an aqueous vehicle or carrier. Such compositions may take any shape: solutions, emulsions, or aqueous gels, and so on.

Within the scope of this invention, the term "aqueous carrier or vehicle" implies any cases where water is practically the only constitutive material of such vehicle as well as those in which water is associated at relatively significant proportions with other substances such as solvents, thickeners, surfactants and so on.

The compositions according to the invention can be applied to the treatment of keratinous fibers in any suitable manner for instance, for hair care a usual method consists of applying a composition according to the invention as described in the Examples for a few minutes to freshly shampooed hair, then rinsing hair with water before combing.

The quantity of the composition according to the invention as applied to the keratinous fibers can vary in significant proportions as desired by the user but generally it must not be lower than 1% of the weight of the keratinous fibers to be treated, and not exceed 20% of this weight.

Efficiency of the tetrapolymers according to the invention in the treatment of keratinous fibers is readily determined by a few simple tests realized from a composition containing them.

Among such tests some are realized on tufts of hair previously shampooed with a commercial shampoo, then treated moist with a composition according to the invention, then one observes visually the effect obtained on hair moist, thereafter dried, both as regards softness, brightness, suppleness, behaviour, non electric property, easiness of doing, and the volume of the obtained hairdo.

Other tests can determine the foaming properties of the compositions according to the invention with the tests described in the Standard ASTM D 1173-53.

Finally, the time stability at the ambient temperature of aqueous solutions containing 0.5% by weight of tetrapolymer according to the invention was investigated by following up the Brookfield viscosity of such solutions stored at daylight at 20° C. for 60 days in the presence of 0.07% by weight of a mixture of known bactericides and fungicides currently used in cosmetology. No significant variations of the Brookfield viscosity of such solutions was noted and furthermore, they remain perfectly limpid.

Other advantages and characteristics of this invention will appear from a study of the following description and the Examples which are given by way of illustration and not at all limitatively.

EXAMPLE 1

Preparation of a cationic ampholytic tetrapolymer, AAM-AMPS-DMAPMA-MAPTAC, 40/20/20/20 in molar proportions.

There is heated from 20° C. to 80° C. in a reactor at the rate of 1° to 1.5° C. per minute in a nitrogen atmosphere an aqueous solution perfectly deoxygenated containing:

29.39 g (0.142 mole) of AMPS,
24.14 g (0.142 mole) of DMAPMA
20.16 g (0.284 mole) of AAM
31.31 g (0.142 mole) of MAPTAC,
0.787 g (3.45 mmoles) of ammonium persulfate,
595 g of water.

Initiation occurs at about 60° C. and when the temperature of the solution reaches 80° C. it is maintained for 1 hour at this temperature, then there is introduced, at 80° C., 0.262 g (1.5 mmole) of ammonium persulfate in solution in 5 g of water and the heating is continued for 1 additional hour at 80° C. and then 30 minutes at 85°–90° C. The medium is then cooled to the ambient temperature, thereafter the pH of the solution is set to 6.5–7.0 with 20% diluted ammonia.

An aqueous solution is thus obtained presenting a Brookfield viscoviscosity as determined at 20° C. at 20 rotations per minute with axis 2, of 0.36 Pa.s and containing by weight 15.5% of a cationic ampholytic tetrapolymer:

AAM-AMPS-DMAPMA-MAPTAC, 40/20/20/20 in molar proportions, and an intrinsic viscosity as determined at 20° C. in a molar solution of sodium chloride of 1.01 dl/g.

EXAMPLES 2-6

By proceeding according to Example 1 but starting from molar proportions of the monomers as given in Table I, aqueous solutions are otained, containing cationic ampholytic water-soluble tetrapolymers with an MA concentration expressed in g per 100 g and determined by drying a test sample of 1 g at 140° C. for 1 hour. These aqueous solutions present a Brookfield viscosity expressed in milli-Pascals/second and determined at 20° C. with a Brookfield viscosimeter provided with the axis 2 rotating at 20 rotations per minute as mentioned in Table V. The intrinsic viscosities [η] of the obtained tetrapolymers are also given in Table I; such viscosities were determined at 25° C. in a molar solutio of sodium chloride The content of residual monomers was determined by conventional dosage of the residual ethylenic bonds; it is expressed in grams per 100 g of the solution.

as a function of the observed effects, the compositions from 1 to 5 have been denoted according to the following code:
excellent: 5
good: 4
average: 3
poor: 2
bad: 1

The obtained results are mentioned in Table III.

Similarly, the compositions have been tested once the hair had been dried and visual observations of these effects were mentioned in Table IV.

Effect of the composition upon moistened hair.

TABLE III

| Tests | Formula No | | | | | | |
|---|---|---|---|---|---|---|---|
| | 8 | 10 | 11 | 12 | 13 | 14 | 15 |
| Easiness of combing | | | | | | | |
| (a) after treatment | 4 | 4 | 2 | 3 | 5 | 4 | 2 |
| (b) after a, then rinsing | 3 | 4 | 3 | 3 | 5 | 3 | 2 |
| Softness of hair | | | | | | | |
| after b | 3 | 3 | 3 | 3 | 4 | 3 | 4 |
| Totals | 10 | 11 | 8 | 9 | 14 | 10 | 8 |

TABLE I

| No | Composition in molar % | | | | MA % | Brookfield viscosity m Pa.s | Intrinsic viscosity dl/g | Residual monomer proportion |
|---|---|---|---|---|---|---|---|---|
| | AAM | AMPS | DMAPMA | MAPTAC | | | | |
| 2 | 75 | 10 | 10 | 5 | 15.4 | 2550 | 1.53 | 0.08 |
| 3 | 70 | 10 | 10 | 10 | 15.3 | 2075 | 1.60 | 0.09 |
| | AAM | AMPS | ADAME | MAPTAC | | | | |
| 4 | 70 | 10 | 10 | 10 | 15.5 | 890 | 1.25 | 0.25 |
| 5 | 70 | 10 | 10 | 10 | 10.5 | 38250 | 4.15 | |
| | AAM | AMPS | ADAME | CHA | | | | |
| 6 | 60 | 10 | 10 | 20 | 15.5 | 2775 | 1.76 | 0.17 |

EXAMPLES 7-15

A—Preparation of Compositions for Treating Hair

From aqueous solutions of cationic ampholytic water-soluble tetrapolymers as described in Examples 1-6, aqueous compositions are prepared, for treating hair, numbered from 7 to 14.

The percentages by weight of active dry materials of the various ingredients in such compositions are mentioned in Table II.

Composition number 15 is a reference composition.

TABLE IV

| Tests | Formula No | | | | | | | | |
|---|---|---|---|---|---|---|---|---|---|
| | 7 | 8 | 9 | 10 | 11 | 12 | 13 | 14 | 15 |
| Easiness of combing | 4 | 4 | 4 | 4 | 4 | 5 | 4 | 3 | 3 |
| Softness | 4 | 4 | 4 | 4 | 4 | 4 | 4 | 4 | 3 |
| Swelling | 4 | 3 | 4 | 4 | 4 | 3 | 4 | 4 | 3 |
| Brightness | 4 | 4 | 4 | 4 | 3 | 4 | 5 | 5 | 3 |
| Non electric property | 4 | 4 | 4 | 4 | 2 | 2 | 5 | 2 | 3 |
| Shaping | 3 | 3 | 3 | 3 | 4 | 5 | 5 | 4 | 4 |
| TOTALS | 23 | 22 | 23 | 23 | 21 | 23 | 27 | 22 | 19 |

TABLE II

| Ingredients | Examples | | | | | | | | |
|---|---|---|---|---|---|---|---|---|---|
| | 7 | 8 | 9 | 10 | 11 | 12 | 13 | 14 | 15 |
| Tetrapolymer | | | | | | | | | |
| ex. 1 | 2.82 | 2.75 | | | | | | | |
| 2 | | | 2.79 | 2.77 | | | | | |
| 3 | | | | | 2.78 | | | | |
| 4 | | | | | | 2.85 | | | |
| 5 | | | | | | | 4.06 | | |
| 6 | | | | | | | | 2.85 | |
| LESA | 30 | 30 | 30 | 30 | 30 | 30 | 30 | 30 | 30 |
| Formaldehyde at 37% | 0.2 | 0.2 | 0.2 | 0.2 | 0.2 | 0.2 | 0.2 | 0.2 | 0.2 |
| Water q.s. for 100 g | 66.98 | 67.05 | 67.01 | 67.03 | 67.02 | 66.95 | 65.74 | 66.95 | 69.80 |
| Total weight | 100.00 | 100.00 | 100.00 | 100.00 | 100.00 | 100.00 | 100.00 | 100.00 | 100.00 |

LESA: sodium laurylethersulfate.

B—Effects on the Compositions Upon Moistened Hair Previously Shampooed, Then on Dry Hair The effects of the compositions in accordance with this invention upon the moistened, previously shampooed, hair were determined by visual examination and, C—Determination of the Foaming Power of the Compositions The foaming power of certain compositions was determined at 40° C. according to Standard ASTM D 1173-53 after dilution of the compositions at 3% by weight in city water. Table V reports the foam heights expressed in centimeters as a function of time expressed in minutes for the tested compositions.

TABLE V

| Formula No | t = 0 | t = 1 min. | t = 5 min. |
| --- | --- | --- | --- |
| 12 | 24 | 22.5 | 22.5 |
| 14 | 22 | 20.5 | 20.5 |
| 15 | 21 | 20 | 19 |

We claim:

1. A cationic ampholytic water-soluble tetrapolymer for cosmetic compositions for treating keratinous fibers, the tetrapolymer having the following general formula:

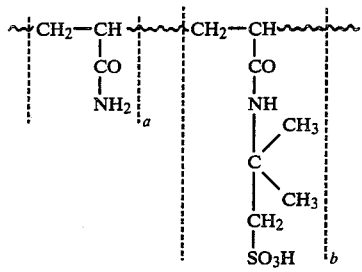

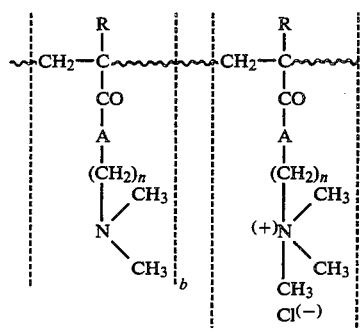

in which A represents an oxygen atom or an NH group, R represents a hydrogen atom or a methyl group when A represents an NH group, and only a hydrogen atom when A represents an oxygen atom, n is equal to 2 when A represents an oxygen and and n is equal to 3 when A represents an NH group, with a, b, c representing the molar percentages of each monomer used and responding to the following relations:

$a + 2b + c = 100$ $30 < a < 75$ $10 < b < 25$ $5 < c < 20.$

2. A cationic ampholytic water-soluble tetrapolymer according to claim 1 resulting from copolymerization of:
   a moles of acrylamide;
   b moles of 2-acrylamido-2-methyl-propane sulfonic acid;
   b moles of a basic monomer selected from the group consisting of
     dimethylaminoethyl acrylate,
     N-(3-dimethylamino-1-propyl)acrylamide, and
     N-(3-dimethylamino-1-propyl)methacrylamide;
   c moles of a cationic monomer selected from the group consisting of
     N,N,N-3-trimethylacrylamido-propanaminium chloride,
     N,N,N-3-trimethylmethacrylamide-propanaminium chloride,
     N,N,N-2-trimethylacryloyloxy-ethanaminium chloride, and
     dimethylaminoethyl acrylate hydrochloride;
   with the following relations:

$a + 2b + c = 100$ $30 < a < 75$ $10 < b < 25$ $5 < c < 20.$

3. A tetrapolymer according to claim 1, containing in molar proportions 75% of acrylamide, 10% of 2-acrylamido-2-methyl-propanesulfonic acid, 10% of N-(3-dimethylamino-1-propyl)-methacrylamide, and 5% of N,N,N-3-trimethylmethacrylamido-propanaminium chloride.

4. A tetrapolymer according to claim 1, containing in molar proportions, 40% of acrylamide, 20% of 2-acrylamido-2-methyl-propanesulfonic acid, 20% of N-(3-dimethylamino-1-propyl)-methacrylamide and 20% of N,N,N-3-trimethylmethacrylamido-propanaminium chloride.

* * * * *